(12) United States Patent
Pintel

(10) Patent No.: US 9,848,790 B2
(45) Date of Patent: Dec. 26, 2017

(54) METHOD FOR MONITORING PRESSURE EXERTED ALONG THE LENGTH OF A BIOLOGICAL CHANNEL

(71) Applicant: Lunguard Ltd., Omer (IL)

(72) Inventor: Ofer Pintel, Matan (IL)

(73) Assignee: Lunguard Ltd., Omer (IL)

( * ) Notice: Subject to any disclaimer, the term of this patent is extended or adjusted under 35 U.S.C. 154(b) by 231 days.

(21) Appl. No.: 14/413,967

(22) PCT Filed: Jul. 7, 2013

(86) PCT No.: PCT/IL2013/050580
§ 371 (c)(1),
(2) Date: Jan. 9, 2015

(87) PCT Pub. No.: WO2014/009950
PCT Pub. Date: Jan. 16, 2014

(65) Prior Publication Data
US 2015/0173634 A1 Jun. 25, 2015

Related U.S. Application Data

(60) Provisional application No. 61/699,326, filed on Sep. 11, 2012, provisional application No. 61/670,179, filed on Jul. 11, 2012.

(51) Int. Cl.
*A61B 5/103* (2006.01)
*A61B 5/03* (2006.01)
(Continued)

(52) U.S. Cl.
CPC ............ *A61B 5/037* (2013.01); *A61B 5/0053* (2013.01); *A61B 5/02007* (2013.01);
(Continued)

(58) Field of Classification Search
CPC ....... A61B 5/021; A61B 5/022; A61B 5/0215; A61B 5/031; A61B 5/03; A61B 5/4528; A61B 5/103; A61B 5/0053
(Continued)

(56) References Cited

U.S. PATENT DOCUMENTS 5,275,169 A 1/1994 Afromowitz et al.
7,947,001 B1 5/2011 Sarvazyan
(Continued)

FOREIGN PATENT DOCUMENTS

CA 1076831 A1 5/1980
JP 2009509713 A 3/2009
(Continued)

OTHER PUBLICATIONS

International Search Report of PCT/IL2013/050580 dated Nov. 4, 2013.
(Continued)

*Primary Examiner* — Daniel Cerioni
(74) *Attorney, Agent, or Firm* — Venable LLP

(57) ABSTRACT

The present invention provides a method for monitoring the actual pressure exerted by the interior wall of a biological channel at different locations along the length of said biological channel. The method comprises: i) introducing into the lumen of the biological channel a device comprising an elongated tube and at least two expandable means located at a predetermined distance on said elongated tube; ii) inflating each of the expandable means to its contact pressure (Pc); and iii) measuring the internal pressure in each expandable means, wherein when said internal pressure is greater than Pc, the actual pressure exerted by the interior wall of the biological channel is equal to the difference between said internal pressure and Pc.

6 Claims, 3 Drawing Sheets

(51) Int. Cl.
- *A61B 5/02* (2006.01)
- *A61B 5/0215* (2006.01)
- *A61B 5/00* (2006.01)
- *A61B 5/20* (2006.01)

(52) U.S. Cl.
CPC .......... *A61B 5/02158* (2013.01); *A61B 5/033* (2013.01); *A61B 5/20* (2013.01); *A61B 5/43* (2013.01); *A61B 5/6853* (2013.01)

(58) Field of Classification Search
USPC ........................................ 600/485, 561, 587
See application file for complete search history.

(56) References Cited

U.S. PATENT DOCUMENTS

| | | |
|---|---|---|
| 7,993,336 B2 | 8/2011 | Jackson et al. |
| 2005/0124920 A1 | 6/2005 | Gregersen |
| 2007/0100333 A1* | 5/2007 | Jackson ................ A61N 1/403 606/41 |
| 2010/0023038 A1 | 1/2010 | Santra et al. |
| 2011/0130650 A1 | 6/2011 | Dayan et al. |

FOREIGN PATENT DOCUMENTS

| | | |
|---|---|---|
| JP | 2011529766 A | 12/2011 |
| WO | 2010/016054 A1 | 2/2010 |

OTHER PUBLICATIONS

Office Action dated Jun. 27, 2017 for JP 2015-521143 (original and translation).

\* cited by examiner

METHOD FOR MONITORING PRESSURE EXERTED ALONG THE LENGTH OF A BIOLOGICAL CHANNEL

FIELD OF THE INVENTION

The invention relates to the medical field and more particularly to a method for monitoring the pressure exerted by the interior wall of a biological channel at different locations along the length of this biological channel.

BACKGROUND OF THE INVENTION

Modern medical devices use expandable means (EM) and in particular inflatable balloons for achieving different operations. Examples of such devices can be found for instance in WO 2010/016054.

WO 2010/016054, which is incorporated herein by reference, relates to an enteral feeding device that enables the administration of nutritive solutions directly into the stomach of a patient. The device disclosed therein significantly reduces the risks of aspirations from the alimentary tract into the respiratory system and allows deglutition of biological fluids secreted in the upper part of the digestive system into the stomach. The middle section of the feeding device of WO 2010/016054 comprises at least three expandable means surrounding a flexible tube, which can be inflated or deflated by introducing or draining a fluid into/from the internal volume of the expandable means. Some of the purposes of the expandable means of the device disclosed in WO 2010/016054 are as follows: 1) blocking the progression of the gastrointestinal fluids in the esophagus, 2) allowing the redirection of the gastrointestinal fluids towards the stomach, and 3) enabling the swallowing of the oropharynx fluids naturally secreted by the patient.

However, there is currently no simple way to determine whether the inflation of an expandable means at a specific location of the lumen of a biological channel (such as in the example above) has an incidence on the pressure exerted by the interior wall of said biological channel at other locations. Thus, it would be useful to have a simple method to monitor the pressure exerted by the interior wall of a biological channel at different locations along the length of the biological channel.

Therefore, it is an object of the present invention to provide a method for monitoring the pressure exerted by the interior wall of a biological channel at different locations along the length of the biological channel.

Further purposes and advantages of this invention will appear as the description proceeds.

SUMMARY OF THE INVENTION

The present invention provides a method for monitoring the actual pressure exerted by the interior wall of a biological channel at different locations along the length of said biological channel, said method comprising:
i) introducing into the lumen of said biological channel a device comprising an elongated tube and at least two expandable means located at a predetermined distance on said elongated tube;
ii) inflating each of the expandable means to its contact pressure (Pc); and
iii) measuring the internal pressure inside each expandable means, wherein when said internal pressure is greater than Pc, the actual pressure exerted by the interior wall of a biological channel is equal to the difference between said internal pressure and Pc.

As used herein, the term "actual pressure" is the pressure exerted by a section of the interior wall of a biological channel towards the lumen of the channel.

As used herein, the term "contact pressure" is the pressure of the fluid in an expandable means necessary to inflate the expandable means and bring it into contact with the wall of the biological channel (i.e. the expandable means is in contact with the interior wall of the biological channel but does not apply any pressure on it).

As used herein, the term "internal pressure" is the pressure of the fluid present in an expandable means at a definite time.

In some embodiments, the device employed in the method of the invention is a disposable device. In specific embodiments, the device comprises at least two expandable means which are located side-by-side on the elongated tube. In some other embodiments, the expandable means are located at a distance of at least 1 cm one to the other on said elongated tube. In one specific embodiment, the device comprises three expandable means, wherein one of the expandable means is used as a blocking means and the two other expandable means are used to monitor the actual pressure exerted by the interior wall of the biological channel. The method of the invention may be used for instance in biological channel belonging to a biological system selected from the group consisting of the blood circulation system, the digestive system, the respiratory system, the urinary system and the reproductive system.

BRIEF DESCRIPTION OF THE DRAWINGS

The above and other characteristics and advantages of the invention will be more readily apparent through the following examples, and with reference to the appended drawings, wherein.

DESCRIPTION

Figure 1:
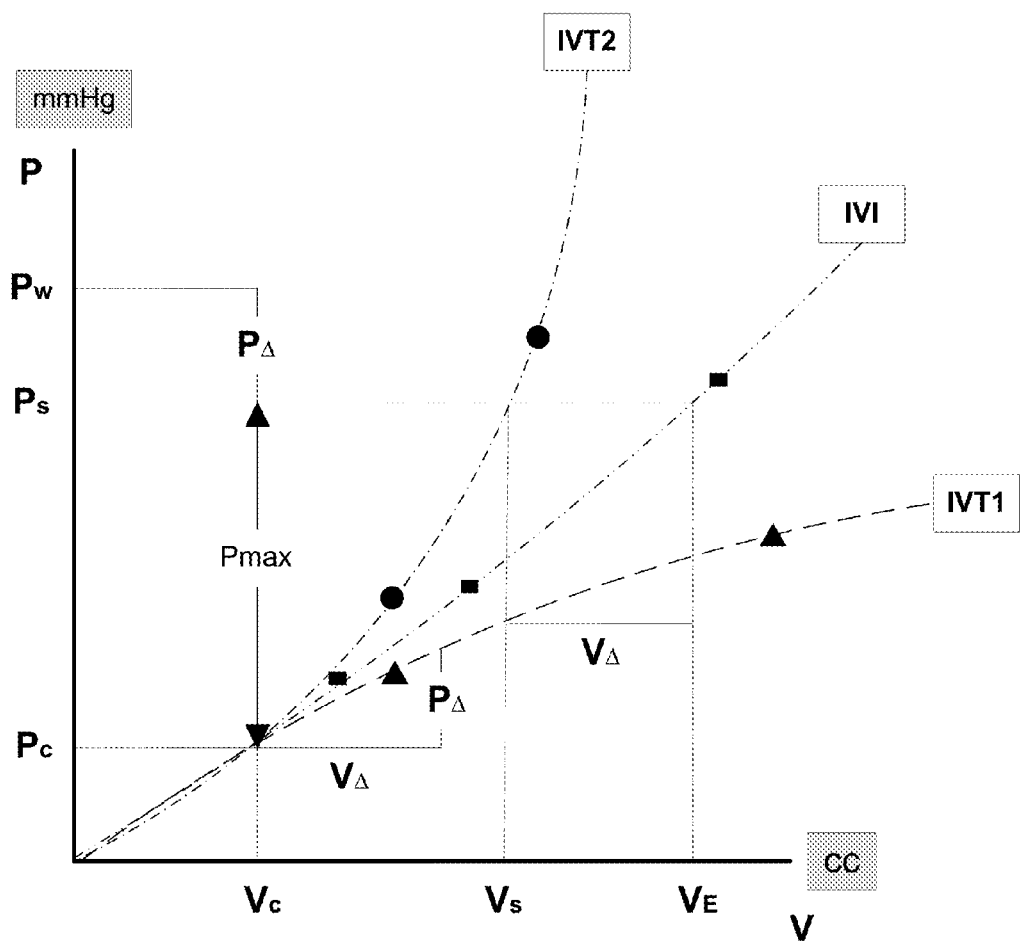
FIG. 1 is a graph showing three calibration curves (pressure measured as a function of volume of fluid injected) obtained for a specific expandable means, as well as the different critical points used in an embodiment of the method of the invention for calibrating this specific expandable means; the first in vitro calibration curve is represented by IVT1 (▲), the second in vitro calibration is represented by IVT2 (●), and the in vivo calibration curve is represented by IVI (■).

The present invention provides a method for monitoring the pressure exerted by the interior wall of a biological channel at different locations along the length of said biological channel. It has been found that the actual pressure exerted by the interior wall of a biological channel at a specific location can be measured by determining the pressure applied on an expandable means after it has been inflated and brought into contact with the wall of the biological channel. The presence of at least two expandable means in the lumen of the biological channel allows real-time monitoring of pressures exerted by the interior wall along the length of the biological channel.

Device Used in the Methods of the Invention

The method of the present invention employs a device having an elongated tube, or an elongated hollow tube, and at least two expandable means localized at different places of this elongated tube. The device is connected to a control and monitoring unit (CMU) which in charge of actuating and monitoring the device by introducing/removing a quantity of fluid to inflate/deflate the expandable means.

The device is placed in the lumen of a biological channel that belongs to the blood circulation system (heart, artery, vein), the digestive system (esophagus, stomach, duodenum, small intestine, large intestine, anus), the respiratory system (trachea, bronchi), the urinary system (kidney, ureter, bladder, urethra) or the reproductive system (vas deferens, ejaculatory duct, vagina, uterus, fallopian tube). Several devices may be connected simultaneously to the CMU and may be implanted in the same biological channel at different positions or in distinct biological systems (e.g. one in the trachea and another in the esophagus). The different devices may be used either sequentially or simultaneously and their actions may be synchronized via the CMU.

Expandable means of said device are inflated/deflated via a fluid channel situated in the elongated tube, preferably in the wall of the elongated tube and connected to the CMU. In case several expandable means are present on the device, each of them comprises a distinct fluid connection to the CMU and is activated independently. A suitable fluid may be in a gaseous or liquid form, for instance air or saline water. The expandable means may have various sizes and shapes according to their intended use, and vary according to the biological channel into which they should be introduced. Physical data related to each one the expandable means of the device of the invention (e.g. size, shape, material, resistance, maximum volume, pressure) are measured during the manufacture and stored into an electronic storage element (e.g. a chip) preferably situated at the proximal end of the device. At the time the device used in the present invention is connected to the CMU, the information relative to each one of the expandable means is automatically transferred to the CMU, enabling the self-calibration of the device once placed in the biological channel. Similarly, data relating to the batch production are stored in the chip and transmitted automatically to the CMU once the device is connected. The device comprises more than one expandable means, either in contact with each other or placed close one to each other (separated by a gap whose size is determined according to the function to be performed by the expandable means), or localized at different positions around the elongated tube. Expandable means are made of different material such as silicon, polyurethane, PVC and alike.

Calibration of the Expandable Means

The maximum pressure that can be applied for a long period of time on epithelial tissues without damaging them is known in the art. In most cases, this pressure should serve as a target pressure or maximum pressure ($P_{Max}$) that can be applied continuously by an expandable means on the interior wall of the channel. However, the pressure of the fluid measured within the expandable means by external pressure sensors does not correspond to the pressure effectively applied by the expandable means on the wall of the biological channel. Indeed, it was found by the inventors that several additional factors should be considered when calibrating the expandable means, such as the pressure developed to inflate the expandable means up to the full contact with the wall of the biological channel (called hereafter the "contact pressure" $P_c$), and additional factors such as the pressure applied to compensate the deformation of the biological channel ($P_A$). The contact pressure $P_c$ depends on severable variables inherent to the expandable means such as the material, thickness, elasticity, diameter, or shape. The pressure $P_A$ merely reflects the pressure which causes the flexible biological channel to enlarge its diameter, but is not a pressure directly applied onto the wall of the channel.

In summary, the pressure relative to the expandable means as measured by the external sensors in the CMU (referred herein as the working pressure ($P_W$)) can be defined as follows:

$$P_W = P_c + P_{Max} + P_A$$

wherein $P_W$ corresponds to the working pressure as measured by the external sensors;

Pc corresponds to the contact pressure, in other words the pressure used to inflate the expandable means and bring it into the full contact with the wall of the channel (no effect on the tissues);

$P_{Max}$ corresponds to the maximum pressure that can be continuously applied on the wall of the biological channel; and $P_A$ corresponds to the pressure due to additional factors, such as the deformation of the biological channel.

The working pressure ($P_W$) should be calibrated for each expandable means independently, so that the pressure continuously applied to the wall of the biological channel by said expandable means does not exceed the maximum pressure ($P_{Max}$) described in the literature, above which damages are made to the tissues.

During the manufacturing process of the device of the invention, two "in vitro" tests are made on the expandable means. The first in vitro test comprises the following steps:

1) the expandable means is deflated and a volume of fluid is gradually injected in the expandable means until a pre-determined volume threshold is reached;

2) the pressure inside the expandable means is recorded as a function of the volume of fluid injected and a calibration curve (IVT1) is recorded; and 3) the recorded data are transferred on a digital media (e.g. electronic chip) associated with the expandable means.

The second in vitro test comprises the following steps:

1) the expandable means is placed in a rigid tubular structure having a diameter corresponding to the target biological channel (e.g. average diameter of an esophagus);

2) the expandable means is deflated and a volume of fluid is gradually injected in the expandable means until a pre-determined volume threshold is reached;

3) the pressure inside the expandable means is recorded as a function of the volume of fluid injected and a calibration curve (IVT2) is recorded; and 4) the recorded data are transferred on a digital media (e.g. electronic chip) associated with the expandable means.

The data recorded are used for determining the working pressure of the expandable means after the in vivo test has been performed.

The in vivo test comprises the following steps:

1) the expandable means is introduced in the lumen of the biological channel of the patient;

2) the expandable means is deflated and a volume of fluid is gradually injected in the expandable means until a pre-determined volume threshold is reached; and 3) the pressure inside the expandable means is recorded as a function of the volume of fluid injected and a calibration curve (IVI) is recorded.

The data obtained from the in vivo test and those obtained from the two in vitro tests are then automatically treated and analyzed via a software program. The data of the three curves are adjusted and the best fit between the three curves is determined (see FIG. 1). By doing so, a characteristic point appears, above which a discrepancy between the values of the pressures obtained in the three different curves is observed. This characteristic point corresponds to the pressure $P_C$ and the volume $V_C$ at which the expandable means comes into full contact with the interior wall of the biological channel/rigid tube. Up to the pressure $P_C$, the pressure measured in the expandable means represents the pressure needed to inflate the expandable means and bring it into full contact with the surrounding wall/tube with no actual pressure effect on the tissue. To the pressure $P_C$, the pressure $P_{Max}$ is added in order to reach a pressure $P_S$. Reporting the value $P_S$ to the calibration curve IVT2 (●) gives a volume $V_S$, which is the volume necessary to apply $P_{Max}$ to the wall of the rigid tube in the second in vitro experiment (as described above). Similarly, reporting the value $P_S$ to the calibration curve IVI (■) gives the volume $V_E$. The difference between the volume $V_E$ and the volume $V_S$ corresponds to a volume $V_A$, which reflects the volume of fluid injected in the expandable means to enlarge the flexible biological channel surrounding it. In order to determine the pressure $P_A$ which is the pressure used to inflate the expandable means in the biological channel until it applies a pressure on the wall, the volume $V_A$ is reported to the calibration curve IVT1 (▲), taking $P_C/V_C$ as a reference (see FIG. 1).

The value of the working pressure $P_W$ is therefore determined as follows:

$$P_W = P_c + P_{Max} + P_A$$

wherein $P_W$ corresponds to the working pressure as measured by the external sensors;

Pc corresponds to the contact pressure, in other words the pressure used to inflate the expandable means and bring it into the full contact with the wall of the channel (no effect on the tissues);

$P_{Max}$ corresponds to the maximum pressure that can be continuously applied on the wall of the biological channel; and $P_A$ corresponds to the pressure due to additional factors, such as the deformation of the biological channel.

As it can be understood from the above, the working pressure $P_W$ is characteristic of a specific expandable means at a certain position within the body of the patient, and corresponds to the optimal working pressure of the expandable means guarantying its full functionality without damaging the surrounding tissues.

Pressure Exerted by the Interior Wall of the Biological Channel

By applying the calibration method described above, the working pressure at which the expandable means is in contact with the wall of the biological channel ($P_C$) can be determined. When the expandable means is inflated at a pressure value of $P_C$, any deformation of the biological channel that would have resulted in the application of a pressure on the material flowing inside the biological channel is applied instead on the inflated expandable means. The pressure exerted on the expandable means can be reported to a central unit and may help monitoring the pressure exerted by the interior wall of a biological channel in real time. This is for instance of particular relevance when monitoring the transpulmonary pressure of a treated patient (see Example 2).

The following examples, which further describe the invention, are offered by way of illustration and are not intended to limit the invention in any manner.

Example 1

Method for Determining the Optimal Working Pressure of an Expandable Means in a Human Esophagus The present example reports the calibration of an expandable means belonging to a device similar to the one described in WO 2010/016054. The pressure inside the expandable means is measured via a control and monitoring unit (CMU) as described in WO 2010/01604. The presently described method aims to determine the optimal working pressure ($P_W$) of the expandable means when located in the esophagus of a treated patient. As discussed above, determining $P_W$ is important to insure that the expandable means achieve the desired function without damaging the tissues of the esophagus during the treatment. In the present example, a maximum pressure $P_{Max}$ of 30 mmHg is to be applied by the expandable means on the internal wall of the esophagus.

Phase 1: In Vitro Calibration Test 1 (IVT1)

1) the expendable means is deflated;

2) the expendable means is gradually inflated by injecting a volume of 0.2 cc of air until a total volume of 5 cc is reached;

3) when a total volume of 5 cc has been injected in the expendable means, the calibration curve reporting the pressure as a function of the volume of air is generated; and 4) the graph obtained in step 3 is recorded on an electronic chip which also contains information relative to the identification number of the expandable means.

This calibration curve corresponds to the "in vitro" test number 1 (IVT1).

Phase 2: In Vitro Calibration Test 2 (IVT2)

1) the expandable means is placed in a rigid tubular structure having a diameter corresponding to the average diameter of an esophagus, namely 14 mm;

2) the expendable means is deflated;

3) the expendable means is gradually inflated by injecting a volume of 0.2 cc of air until a total volume of 5 cc is reached;

4) when a total volume of 5 cc has been injected in the expendable means, the calibration curve reporting the pressure as a function of the volume of air is generated; and 5) the graph obtained in step 4 is recorded on an electronic chip which also contains information relative to the identification number of the expandable means.

This graph corresponds to the "in vitro" test number 2 (IVT2).

Phase 3: In Vivo Calibration (IVI)

1) the expandable means is placed in the patient's esophagus;

2) the expendable means is deflated;

3) the expendable means is gradually inflated by injecting a volume of 0.2 cc of air until a total volume of 5 cc is reached;

4) when a total volume of 5 cc has been injected in the expendable means, the calibration curve reporting the pressure as a function of the volume of air is generated; and 5) the graph obtained in step 4 is recorded and stored in the CMU.

Phase 4: Adjusting the Calibration Curves 1) the expandable means is identified via its identification number by the CMU;

2) the CMU is importing the data corresponding to the two in vitro tests performed in Phase 1 and Phase 2 described above;

3) a software present in the CMU is adjusting the 3 graphs obtained during Phases 1-3 (e.g. by calculating and comparing the derivative of each point of the graphs for a same specific volume);

4) once adjusted, the system determines the pressure corresponding to the pressure at the contact point of the expandable means on the internal esophagus wall/rigid tube wall ($P_C$).

Phase 5: Determining the Optimal Working Pressure 1) a pressure value $P_S$ is determined by adding the pressure $P_{Max}$ (30 mmHg) to the pressure $P_C$ (in this case 10 mmHg).

2) the pressure $P_S$ is reported on the calibration curve obtained from the data of the second in vitro experiment to find $V_S$;

3) the pressure $P_S$ is reported on the calibration curve obtained from the data of the in vivo experiment to find $V_E$;

3) the volume $V_A$ is calculating by the difference $V_E - V_S$;

4) the value of $V_A$ is reported on the calibration curve obtained from the data of the first in vitro experiment and the pressure $P_A$ is determined; and 5) eventually, the optimal $P_W$ is determined by effecting the following operation:

$$P_W = P_C + P_{MAX} + P_A$$

In a particular case (data not shown), the pressure at the contact point ($P_C$) has been determined at 11 mmHg, $P_{Max}$ at 30 mmHg and $P_A$ at 11 mmHg. Therefore, the optimal working pressure $P_W$ in this case has been set to 52 mmHg. In conclusion, when this specific expandable means is inserted inside the esophagus, the working pressure should be about 52 mmHg so that said expandable means effectively applies a continuous pressure on the interior wall of the esophagus of about 30 mmHg, effectively closing the lumen space without damaging the surrounding tissues.

Example 2

Method for Real-Time Monitoring of the Transpulmonary Pressure

Ventilated patients in the intensive care unit are often needed to be monitored for their esophageal pressure during ventilator setting especially during peep adjustment. Pleural pressure can be measured via an esophageal balloon catheter and allows for calculation of the transpulmonary pressure which is the difference between the alveolar pressure (the pressure measured at the airway opening when flow is stopped) and pleural pressure. The measurements are done in the upright position and the expandable means is placed in lower third of the esophagus. Cardiac oscillations are ignored. Because the pressure of an expandable can be measured, the esophageal pressure applied on the expandable can be determined by using the expandable means as a manometer.

In the present example, a device similar to the one in WO 2010/016054 is employed in the esophagus of a patient. All three balloons are deflated and then inflated simultaneously to reach their respective contact pressures $P_C(1)$, $P_C(2)$ and $P_C(3)$. As it can be understood from the description, the values $P_C(1)$, $P_C(2)$ and $P_C(3)$, while similar in some cases, are usually distinct since each one of them corresponds to a specific expandable means (having inherent properties) at a specific position of the esophagus. The transpulmonary pressure is calculated as follows:

$$P_{TP} = P_{AW} - P_{ES}$$

wherein $P_{TP}$ corresponds to the transpulmonary pressure;

$P_{AW}$ corresponds to the tracheal air pressure; and $P_{ES}$ corresponds to the esophageal pressure with $P_{ES} = P_M - P_C$, wherein $P_M$ corresponds to the pressure measured within the expendable means; and $P_C$ corresponds to the contact pressure of the same expandable means.

Figure 2:
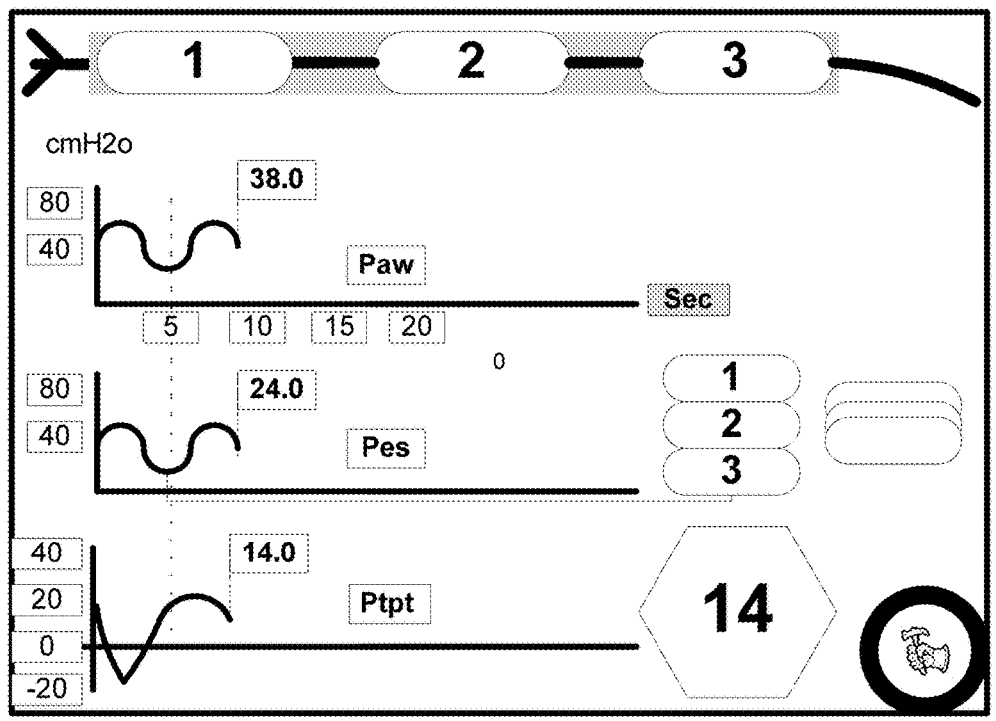
FIG. 2 is a scheme representing an embodiment of a method for the real-time monitoring of the transpulmonary pressure with an expandable means; PTP corresponds to the transpulmonary pressure; PAW corresponds to the tracheal air pressure; and PES corresponds to the esophageal pressure.

As shown in FIG. 2, the tracheal air pressure ($P_{AW}$) is obtained from the data transferred by the tracheal tube. The esophageal pressure ($P_{ES}$) is determined in real-time by measuring at least one of the pressure values of expandable means 1-3, which have been inflated at their respective contact pressure and are used to measure the pressure variations in the lumen of the esophagus. The average of the values reported by the expandable means (or any other combinations) is also considered as a possible embodiment. In the present example (FIG. 2), $P_{AW}$ as measured is 38 cmH$_2$O and $P_{ES}$ is the average value reported by the three expandable means and corresponds to 24 cmH$_2$O. Therefore, the transpulmonary pressure $P_{TP}$ corresponds in this case to 14 cmH$_2$O (or 19 mmHg, when considering that 1 cmH$_2$O=1.359 mmHg).

It is clear from the above that the present method allows real-time monitoring of the transpulmonary pressure via the use of at least one expandable means placed in the esophagus and further data obtained from a tracheal tube.

Although embodiments of the invention have been described by way of illustration, it will be understood that the invention may be carried out with many variations, modifications, and adaptations, without exceeding the scope of the claims.

Example 3

Examples of Devices Used in the Method of the Invention

Figure 3A:
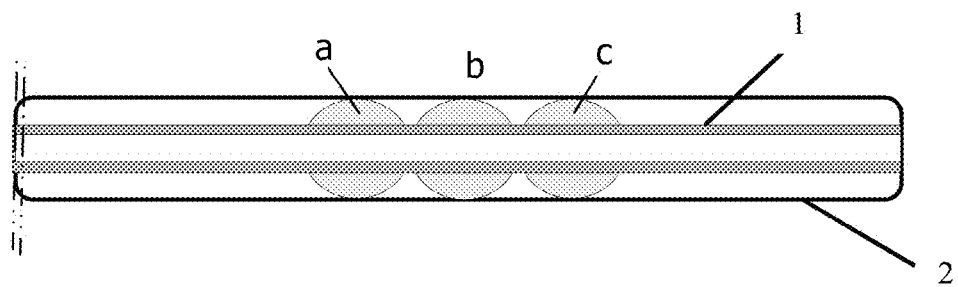
FIG. 3A-3C are schemes representing various embodiments of the device used in the methods of the invention; Legend: a, b, and c—three distinct expandable means; 1—elongated tube; 2—biological channel interior wall.

In a first example (FIG. 3A), the device used in the present invention comprises three side-by-side balloons that are inflated/deflated according to a predetermined cycle controlled by the CMU. The direction of the fluids in the lumen (i.e. between the device and the internal wall of the biological channel) wherein the device is introduced depends on the inflation/deflation cycle profile of the balloons (left-to-right or right-to-left, constant direction or alternate direction). Each of the balloons are used to block the fluids in the lumen, accelerate the flow of the fluids, or monitor local pressures (e.g. pressure exerted by the surrounding fluids and/or pressure of the internal wall of the lumen).

Figure 3B:
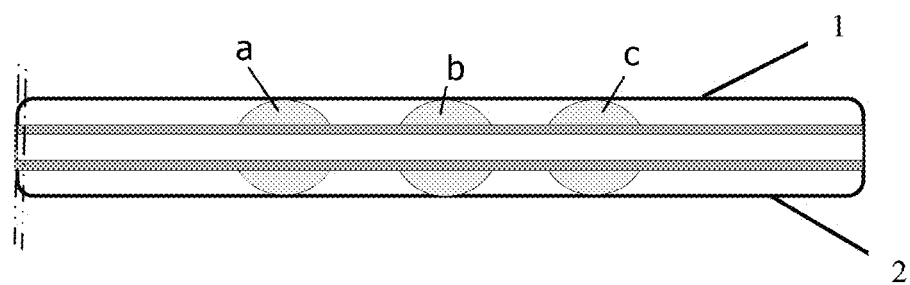

In a second example (FIG. 3B), the device comprises three separated balloons. One of the balloons is used as a blocking means while the two others are used as sensors to determine the properties of the internal wall of the lumen (e.g. flexible/tough tissue, diameter of the lumen at a specific position) and to send the information to the CMU.

Figure 3C:
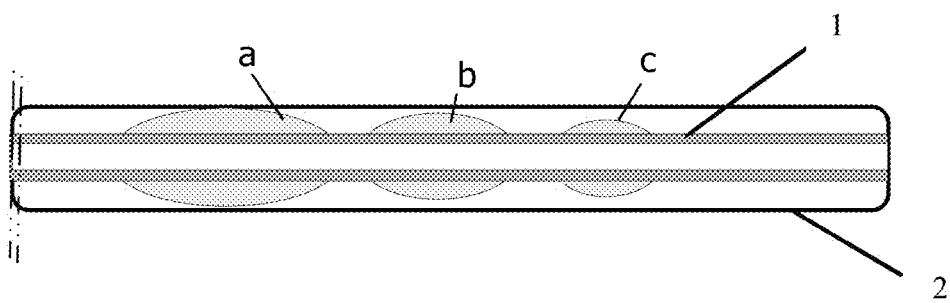

In a third example (FIG. 3C), the device comprises three balloons having different sizes, one of its functions being to gradually enlarge the diameter of the lumen at a predetermined position by pushing against and stretching the surrounding tissues, and measuring the pressure exerted by the interior wall of the biological channel at each specific location.

All the above description and examples have been provided for the purpose of illustration and are not intended to limit the invention in any way.

The invention claimed is:

1. A method for determining for each one of at least two expandable balloons located at different locations along a length of an interior of a biological channel a specific optimum working pressure $P_W$ of fluid used to inflate each one of the at least two expandable balloons, wherein, when each expandable balloon is inflated each expandable balloon's specific $P_W$, each balloon effectively applies a continuous pressure on an interior wall of the biological channel, effectively closing a lumen space without damaging surrounding tissues;

wherein the method is carried out using an apparatus comprising:
a) an elongated tube comprising:
    i) the at least two expandable balloons located at predetermined locations on the elongated tube;
    ii) a distinct fluid connection coupled to each expandable balloon; and
    iii) an electronic storage element comprising physical data related to each one of the expandable balloons, data related to batch production of the elongated tube, and, for each of the expandable balloons, a first and a second calibration curve of pressure inside the expandable balloon as a function of a volume of fluid injected into the expandable balloon through a fluid channel;
    wherein the first and second calibration curves for each expandable balloon are generated and the physical data and the two calibration curves are transferred to the electronic storage element during a manufacturing process of the apparatus; and
b) a control and monitoring unit (CMU) configured to actuate and monitor the apparatus by introducing and removing a quantity of fluid to respectively inflate and deflate each of the expandable balloons, to measure the internal pressure in each of the expandable balloons, to generate an in vivo calibration curve; and to utilize the first and second calibration curves in combination with the in vivo calibration curve to determine the optimal value of $P_W$ for each of the expandable balloons;

the method comprising:

a) transferring data and the first and second calibration curves for each expandable balloon from the electronic storage element on the elongated tube to the CMU;
b) introducing the elongated tube into the biological channel;
c) activating the CMU to deflate each of the expandable balloons;
d) activating the CMU to inject fluid separately into each of the expandable balloons to gradually inflate each of them until a predetermined volume of fluid has been injected into each of the expandable balloons;
e) activating the CMU to generate, record, and store the in vivo calibration curve for each of the expandable balloons that shows a relationship between the internal pressure in each of the expandable balloons as a function of the volume of fluid injected into each of the expandable balloons during the previous step;
f) activating the CMU to adjust and obtain a best fit between the first, second and in vivo calibration curves from which a pressure $P_C$, which corresponds to a pressure at a contact point of the expandable balloon on the internal wall of the biological channel and a pressure $P_A$, which corresponds to a pressure due to deformation of the biological channel are determined; and
g) activating the CMU to determine $P_W$ as follows:

$$P_W = P_C + P_{MAX} + P_\Delta$$

wherein $P_{MAX}$ corresponds to a known maximum pressure that can be continuously applied on the wall of the biological channel.

2. A method according to claim 1, wherein the apparatus is a disposable apparatus.

3. A method according to claim 1, wherein said expandable balloons are placed side-by-side on said elongated tube.

4. A method according to claim 1, wherein said expandable balloons are distant by at least 1 cm one to the other on said elongated tube.

5. A method according to claim 1, wherein the apparatus comprises three expandable balloons, wherein one of the expandable balloons is used as a blocking balloon and the two other expandable balloons are used to monitor the actual pressure exerted by the interior wall of the biological channel.

6. A method according to claim 1, wherein the biological channel belongs to a biological system selected from the group consisting of the blood circulation system, the digestive system, the respiratory system, the urinary system and the reproductive system.

* * * * *